United States Patent [19]

Matthews

[11] Patent Number: 5,269,304
[45] Date of Patent: Dec. 14, 1993

[54] ELECTRO-THERAPY APPARATUS

[76] Inventor: Tony Matthews, 16, Brookleigh Rd., Withington, Manchester, England, M20 9NZ

[21] Appl. No.: 754,675

[22] Filed: Sep. 4, 1991

[30] Foreign Application Priority Data

Mar. 4, 1989 [GB] United Kingdom ............... 8904998

[51] Int. Cl.$^5$ .............................................. A61N 1/00
[52] U.S. Cl. ......................................... 607/46; 607/67; 607/76; 607/148
[58] Field of Search ................... 128/419 R, 421, 783, 128/784, 787, 796, 785

[56] References Cited

U.S. PATENT DOCUMENTS

| | | | |
|---|---|---|---|
| 4,572,214 | 2/1986 | Nordenström et al. | 128/785 |
| 4,637,405 | 1/1987 | Brenman et al. | 128/787 |
| 4,841,973 | 6/1989 | Stecker | 128/421 |
| 4,863,157 | 9/1989 | Mendel et al. | 128/421 |
| 4,895,154 | 1/1990 | Bartelt et al. | 128/421 |
| 4,924,880 | 5/1990 | O'Neill et al. | 128/787 |

*Primary Examiner*—William E. Kamm
*Assistant Examiner*—George Manuel
*Attorney, Agent, or Firm*—Brooks & Kushman

[57] ABSTRACT

An electro-therapy apparatus includes at least two electrodes adapted to feed oscillating current to selected sites on or beneath the epidermal or mucous surface remote from a treatment site. A common return electrode is provided at the treatment site which is subjected to the sum of the currents from the two feed electrodes. The feed electrodes may be contact feed electrodes or capacitative feed electrodes. The feed electrodes may operate at different frequencies so that the treatment site is stimulated by the beat frequency. This may be at or about 80 or 130 Hz, if an anaesthetizing effect is required.

25 Claims, 4 Drawing Sheets

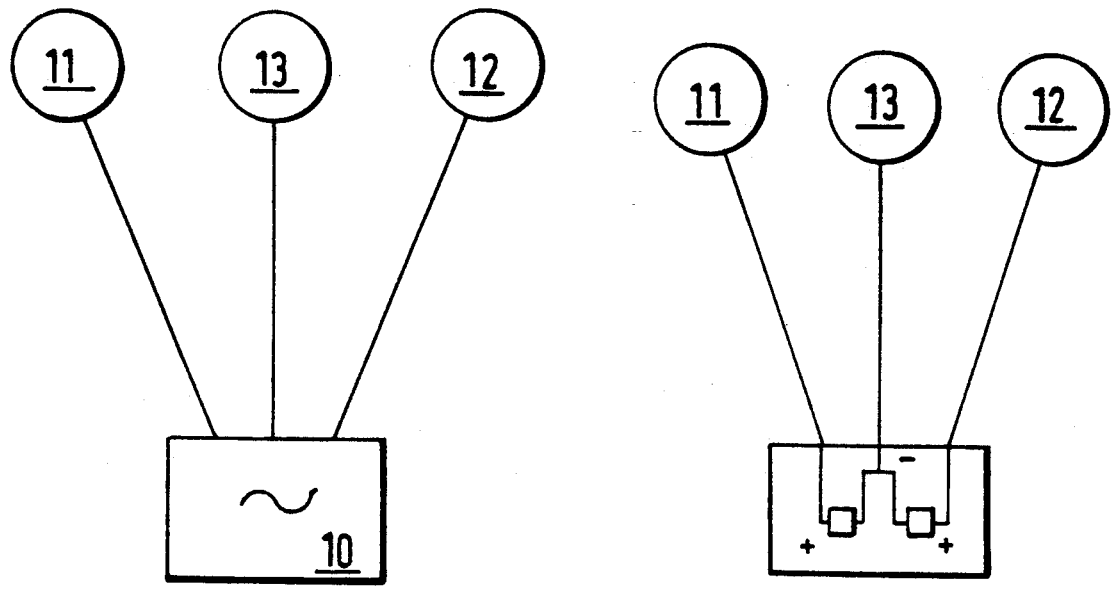
Fig.1.
Fig.3.
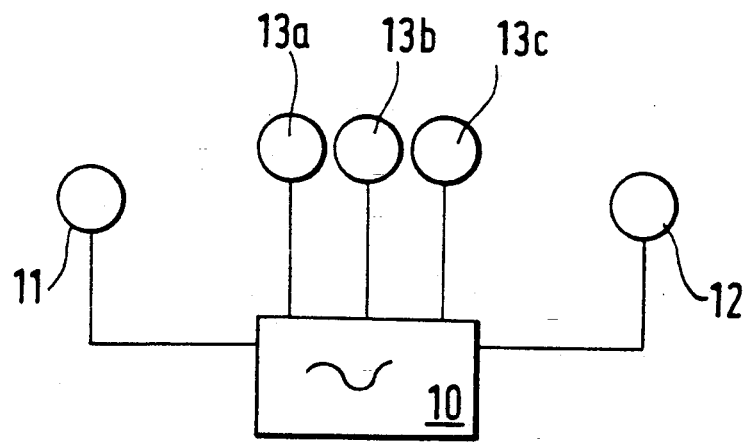
Fig.2.

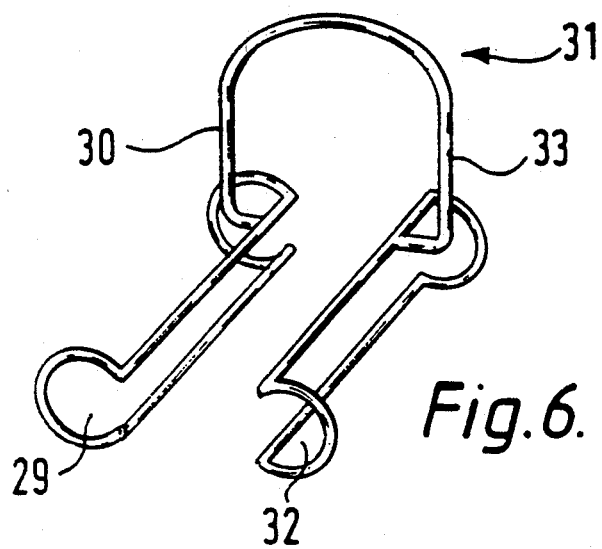
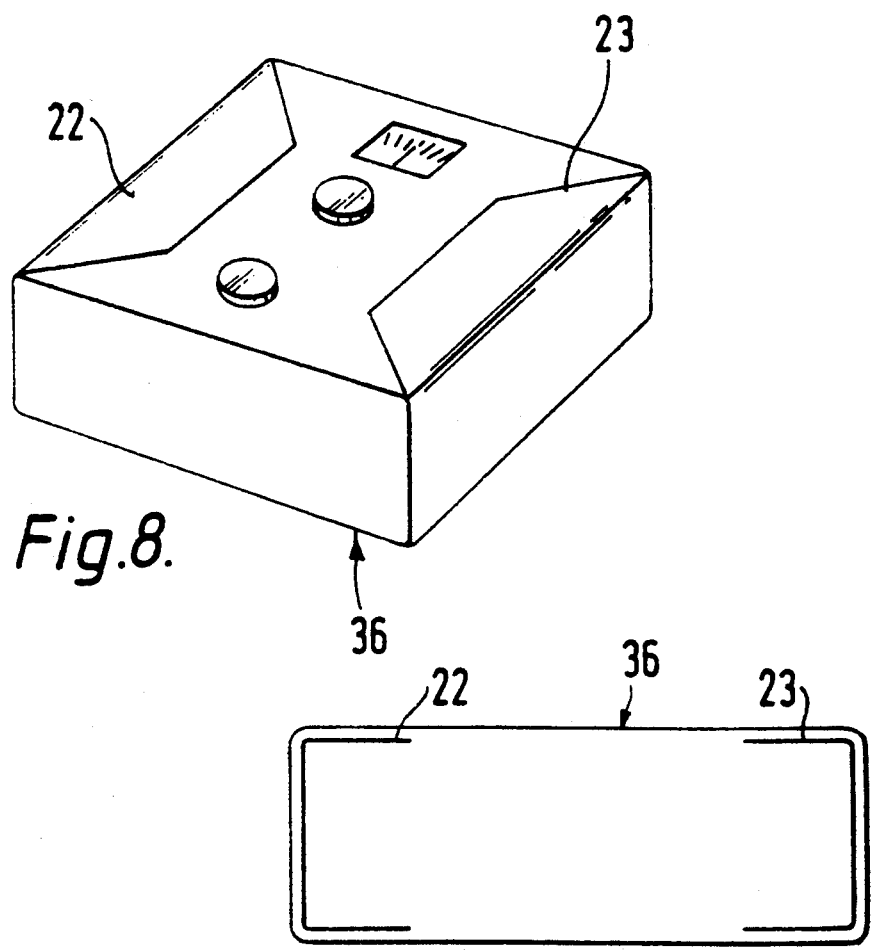

ELECTRO-THERAPY APPARATUS

TECHNICAL FIELD

This invention relates to electro-therapy apparatus, and more particularly, though by no means exclusively, anaesthetizing apparatus capable of application for relief of pain arising from a temporary or chronic condition or during surgery.

BACKGROUND ART

It is well known that application of electro-therapy at frequencies up to about 250 Hz is efficacious in relieving pain. However, current at these frequencies tends to flow between surface electrodes in the epidermal surface with little or no penetration of the underlying tissues. As a result the technique, known as TENS or transcutaneous nerve stimulation, is of limited application.

DISCLOSURE OF INVENTION

It is one object of the present invention to provide electro-therapy apparatus which can apply therapeutic electrical current to more deeply located areas of the body, without any requirement for any invasive or surgically intrusive device.

It is a further object of the present invention to sum relatively low currents at a specific treatment site in order to accurately target the electro-therapeutic effect.

According to a first aspect of the present invention there is provided electro-therapy apparatus comprising a plurality of electrodes adapted to feed respective oscillating or pulsing electric currents to a selected feed site or sites on or beneath an epidermal or mucous surface and at least one return electrode common to the feed electrodes and adapted to be positioned on or beneath an epidermal or mucous surface, local to the treatment site or sites.

Although apparatus of the present invention may be adapted for penetrative or invasive operation, preferred apparatus of the invention is adapted for non-penetrative or non-invasive operation. Thus, feed electrodes may suitably be adapted to feed respective oscillating or pulsing electric currents to a selected feed site or sites on the epidermal or mucous surface, and a return electrode or electrodes may also be adapted to be positioned on an epidermal or mucous surface, local to a treatment site or sites.

Suitably, for convenience, the feed electrodes may be located remotely from the site or sites to be treated, in use, and may be adapted to be so located.

A suitable oscillating or pulsing electric current may be effectively a pulsed d.c. current, that is, with only positive voltage in the cycle. It may alternatively be an alternating current, that is, a current with positive and negative voltages in the cycle. The wave form itself is not believed to be critical, though sinusoidal, square wave and sawtooth forms are preferred.

A preferred current is an alternating current of sinusoidal or square-wave form.

There may be a plurality of return electrodes common to the feed electrodes and means for switching the return electrodes into circuit sequentially.

One or more feed electrodes may be adapted to contact the person undergoing electro-therapy ("contact feed electrode(s)") or may be adapted to provide capacitative feed ("capacitative feed electrode(s)"). Thus, a capacitative feed electrode may comprise a capacitor conductor (one "plate" of a capacitor), the other capacitor conductor, (the other "plate" of the capacitor) being the tissues of a patient, with the dielectric insulator therebetween being air, dead skin, and even, in certain embodiments, an insulating casing for the electro-therapy apparatus. The "plate(s)" could be within the casing or be external, e.g. comprised in a patients' chair, for example a dental chair.

Capacitative feed electrodes are inherently safe, in the event of a short-circuit, and against overloading, and are preferred.

Two feed electrodes may supply current at or equal or, preferably, at different frequencies.

Preferably, two feed electrodes supply current at different frequencies, such that a therapeutic beat frequency is produced. Such a frequency may suitably be up to about 250 Hz, for example in the range about 60 to about 150 Hz and may preferably be at or about 80 or 130 Hz.

Each of two feed electrodes may operate at a frequency up to about 200 KHz, for example in the range about 1 KHz to about 200 KHz. When contact feed electrodes are employed they may suitably operate at a frequency in the range of about 4 to 5 KHz, whereas when capacitative feed electrodes are employed much higher frequencies may be desirable.

Preferably, two feed electrodes may each supply alternating current of sinusoidal or square-wave form.

One or both of two feed electrodes may operate on a varying frequency. This may be effected automatically, by "sweeping" the frequency. It may be under the control of the patient, who may vary one or more frequencies to provide the perceived optimal therapeutic effect.

Feed electrodes may operate intermittently.

The apparatus may be provided with warning means, preferably warning of power failure or malfunctioning of the apparatus.

Contact feed electrodes may be incorporated in one or two pistol grips adapted to be grasped by the patient to be treated.

Suitably, there may be provided two feed electrodes only.

Preferably, there is provided a single return electrode only.

Suitably, the summated area of the feed electrodes exceeds, preferably to a substantial extent, for example by a factor of more than 4, and suitably, for many uses, to a very substantial extent, for example by a factor of more than 100, the contact area of the return electrode or the summated contact area of the return electrodes, when there is more than one (with reference to the feed and return electrode(s) operational at any given moment). Thus, the apparatus may provide a relatively intense current locally to a site being treated. Indeed, the return electrode could be of micropipette or needlepoint form, so as to provide targeted electro-therapy on the cellular level e.g. "cyto-electronically targeted analgesia" (CETA).

The apparatus may comprise a casing which houses e.g. the generating apparatus, which casing may itself comprise a contact feed electrode or electrodes. In such an instance, the casing may be held by a patient in use. The casing may comprise two areas, for example handles which act as respective contact feed electrodes, which a patient may grasp with the hands. Alternatively, the casing could be of an insulating material acting as a dielectric, e.g. plastics, and capacitative feed electrodes could be located within the casing. Alternatively, capacitative feed electrodes could be located externally of the casing.

In accordance with a further aspect of the present invention, there is provided electro-therapy apparatus (optionally but not necessarily in accordance with the first or any other aspect of the present invention) having a casing which itself comprises one or contact feed electrodes, or within which is located one or more capacitative feed electrodes.

A return electrode is preferably a contact feed electrode, to provide accurate targeting, and may be in the form of a disc, band, probe, micropipette, needlepoint or any other form appropriate to the type of electro-therapy which it is desired to provide and/or the medical context.

For dental operation, the apparatus may comprise a return electrode which is adapted to be positioned on the gum adjacent a tooth to be treated. It may be of cylindrical form comprising a conductive material. It may suitably have a conductive zone at a localized position on its peripheral surface. The electrode may suitably be carried by one limb of a U-shaped clip.

An electrode as described in the previous paragraph may comprise a portion which is of conductive material, for example a conductive elastomeric or plastics material, which may be fitted in place in a non-conductive material, for example a non-conductive elastomeric or plastics material, to make a composite body of generally cylindrical form, preferably circularly cylindrical, which may be fitted into a conventional U-shaped clip having opposed holder portions at the distal ends of the respective limbs, for retaining respective cylindrical bodies.

In accordance with a further aspect of the present invention there is provided an electrode as defined in either or both of the previous paragraphs (optionally but not necessarily for use in relation to the apparatus of the first or any other aspect of the present invention).

In accordance with a further aspect of the present invention, there is provided electro-therapeutic apparatus (optionally but not necessarily in accordance with the first or any other aspect of the present invention) having a feed electrode remotely located from a treatment site and a return electrode at or closely adjacent to the treatment site. Thus, in the context of oral use, for example in dentistry, a return electrode may be located in the mouth and a feed electrode may be located outside the mouth, for example at the hand or arm.

In accordance with a further aspect of the present invention, there is provided electro-therapy apparatus (optionally but not necessarily for use in relation to the apparatus of the first or any other aspect of the present invention), for providing a targeted therapeutic effect, which apparatus comprises one or more feed electrode(s) and one or more return electrode(s), wherein the area of the feed electrode, or summated area of the feed electrodes, when there is more than one, exceeds the area of the return electrode, or the summated area of the return electrodes, when there is more than one (with reference to the electrodes which are operational at any given moment).

In accordance with a further aspect of the present invention, there is provided a method of therapeutic treatment of a patient, using any of the apparatus as herein described.

The above objects and other objects, features, and advantages of the present invention are readily apparent from the following detailed description of the best mode for carrying out the invention when taken in connection with the accompanying drawings.

BRIEF DESCRIPTION OF THE DRAWINGS

FIG. 1 shows a diagrammatic representation of a first embodiment of an electro-therapy apparatus constructed in accordance with the present invention;

FIG. 2 shows a diagrammatic representation of a second embodiment of the electro-therapy apparatus constructed in accordance with the present invention;

FIG. 3 shows a diagrammatic representation of a third embodiment of the electro-therapy apparatus constructed in accordance with the present invention;

FIG. 6 shows in perspective view a dental spring clip for retaining the return electrode of FIG. 5d;

FIG. 8 shows in perspective view the casing of apparatus of the invention, which provides two external feed electrodes;

FIG. 10 shows in diagrammatic cross-sectional view the casing of apparatus of the invention, with two internal capacitative feed electrodes.

BEST MODE FOR CARRYING OUT THE INVENTION

Figure 4:
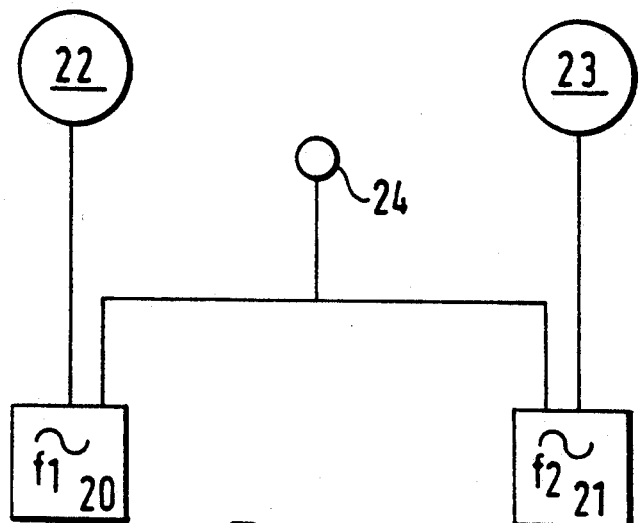
FIG. 4 shows a diagrammatic representation of a fourth embodiment of the electro-therapy apparatus constructed in accordance with the present invention.

Referring firstly to FIG. 1, it will be seen that single electrical oscillator 10 is connected with two contact feed electrodes 11 and 12 and a common contact return electrode 13. In this embodiment, the electrodes 11 and 12 are adapted to be positioned on the epidermal surface to either side of the site to be treated and the return electrode 13 is positioned on such site. The currents flowing from the electrodes 11 and 12 combine in the vicinity of the electrode 13 to give an intensity efficacious for the required treatment whilst currents flowing in the rest of the body are of higher frequency and/or lower intensity, and therefore less interactive with body tissues.

In the arrangement of FIG. 2, wherein like parts are indicated with like reference numerals, the single return electrode 13 is replaced with, in this particular embodiment, three return electrodes 13a, 13b and 13c which are positioned at three discrete treatment sites. A switching circuit (not shown) switches the current sequentially between the three return electrodes. It should be noted that the diagrammatic drawing in FIG. 2 depicts the relative contact areas of the electrodes accurately and that, because only one return electrode is operational at a time, then the summated area of the feed electrodes is approximately double the contact area of return electrode which is operational at any given time.

In the embodiments of FIGS. 1 and 2, the feed electrodes supply alternating current to a patient, the respective signals being of identical wave form, in phase with each other. Summation of the signals is expected to occur.

FIG. 3 shows a circuit analogous to that of FIG. 1, but providing pulsed d.c. signals.

Referring now to FIG. 4, it will be seen that the apparatus comprises two electrical oscillators 20 and 21 arranged to operate at different frequencies $f_1$ and $f_2$ respectively.

The oscillator 20 is connected to a contact fee electrode 22 whilst the oscillator 21 is connected to a contact feed electrode 23. Both oscillators 20 and 21 are connected to a common contact return electrode 24. Return electrode 24, as shown schematically, is substantially smaller in area then feed electrodes 22,23 so as to provide targeted and specific electro-therapy.

The two oscillators 20 and 21 each operate at a frequency in the range of from 4 KHz to 5 KHz but such that the difference between the frequencies ($f_1$-$f_2$) is in the range of from 70 Hz to 150 Hz and preferably at or near 80 Hz or 130 Hz.

At these frequencies, the current penetrates the body tissues as it flows between the electrodes.

In the specific region of the common electrode 24 the two currents interfere to provide stimulation at the beat frequency ($f_1$-$f_2$) and provide the anaesthetizing effects, especially associated with frequencies of or about 80 Hz or 130 Hz.

The electrodes 22 and 23 are attached to the body at positions removed from the treatment site and the electrode 24 is attached or positioned on an epidermal or mucous membrane surface proximate the treatment site.

It will be understood that the electrodes 22 and 23 need not be of special design, and may therefore be conventional conducting rubber discs which can be strapped, for example, to the wrists or ankles.

The common electrode 24 will be generally selected to be suited to the site where it is to be applied.

Figure 5A:
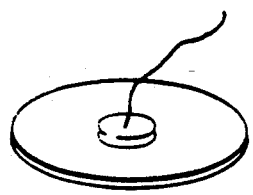
FIGS. 5a–5d shows in perspective views different kinds of return electrode for use in the electro-therapy apparatus of FIGS. 1 to 4.
Figure 5B:
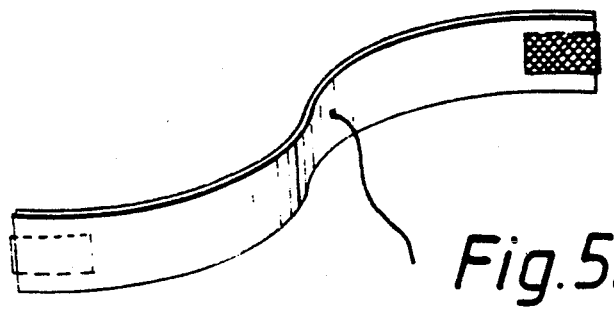
Figure 5C:
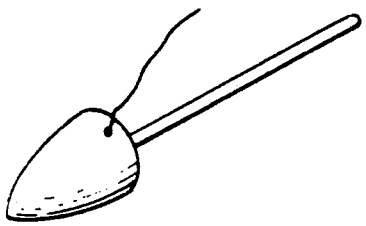

Thus, it may be in the form of a disc (see FIG. 5a) for application to a localized epidermal region. It may be in the form of a flexible band fitted with Velcro ® fasteners (see FIG. 5b) for encircling a joint such as the knee or elbow. Or it may be in the form of a probe (see FIG. 5c) for application to a site on the mucous membrane for example in the mouth or rectum, or a micropipette or needlepoint.

Figure 5D:
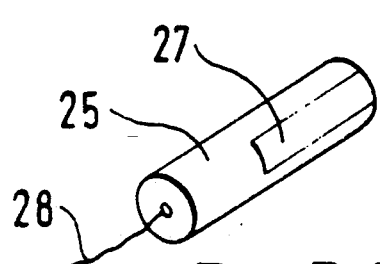

FIG. 5d shows an electrode suited for dental work. It comprises an insulating body 25 of an elastomeric material, circularly cylindrical in shape but having a surface slot formed therein into which a tongue 27 of a conductive elastomeric material is fitted. The conductive tongue 27 is in contact with a conductive wire 28. In use, the composite cylindrical body is carried by a holder 29 formed at the end of one limb 30 of a U-shaped spring clip 31 (FIG. 6), adapted to hold the electrode against the gum adjacent a tooth to be treated. The corresponding holder 32 at the end of the other limb 33 is for a cylindrical wadding body (not shown). In a similar embodiment, the whole cylindrical body 25 may be of conductive material.

More specialized probes enabling access to deeper locations in the alimentary canal are of course possible.

Figure 7:
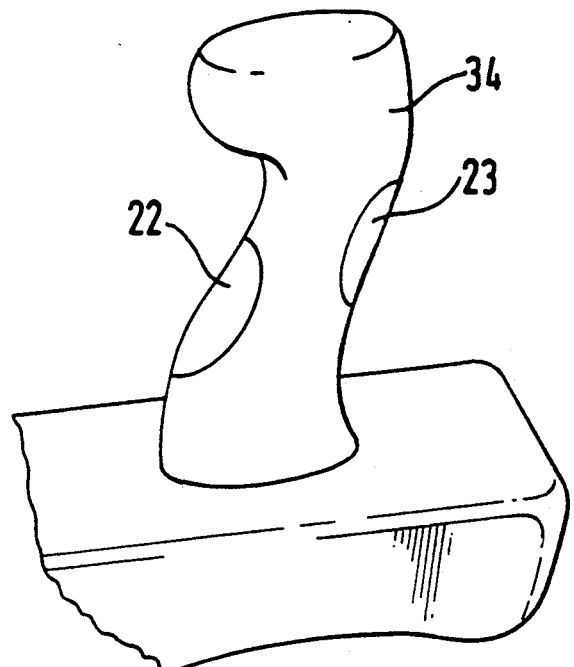
FIG. 7 shows in perspective view a pistol grip incorporating a pair of feed electrodes.

The feed electrodes 22 and 23 may conveniently be located in a pistol grip 34 (see FIG. 7) mounted, for example, on the arm 35 of a dental chair, and adapted to be grasped by the patient to be treated.

In the embodiment shown in FIG. 8, the electrical circuitry is housed in a casing 36 which carries, on its external surface, two plates 22, 23 shaped around respective edges of the casing, located so as to be gripped by the patient during a dental procedure, which handles are the two feed electrodes of the apparatus.

Figure 9:
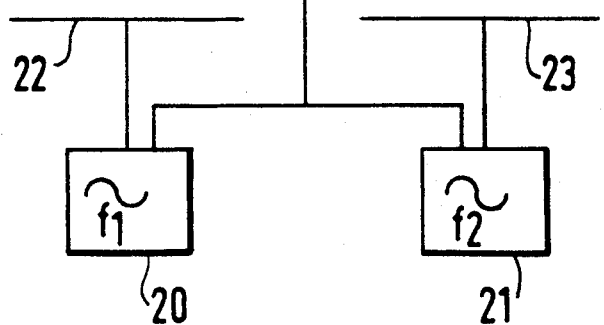
FIG. 9 shows in diagrammatic representation a fifth form of apparatus, providing capacitative feed electrodes.

FIG. 9 shows analogous but preferred apparatus to FIG. 4, but wherein capacitative feed electrodes 22, 23 are employed. Such electrodes may, for example, be located inside an insulating casing of the apparatus and the other "plate" of the capacitor is conductive body tissue fluid.

In the embodiment of FIG. 9, the capacitative feed electrodes 22, 23 may be in the form of conductive plates, for example of a metallic or conductive rubber material. In this embodiment, frequencies $f_1$ and $f_2$ may be considerably higher than in the case of the FIG. 3 embodiment. For example, $f_1$ could be 50130 Hz and $f_2$ could be 50000 Hz.

In the embodiment of FIG. 10, a pair of capacitative feed electrodes 22, 23 are shown located within the plastics insulating casing 36 of the apparatus.

In other embodiments, capacitative feed electrodes could be external to the casing. For example, they could be located within a dental chair, or in a cover over the dental chair.

Preliminary tests using the apparatus of the present invention have proved promising particularly for dental surgery where numerous deep filings have been carried out using the apparatus of the invention as the sole anaesthetizing means. The electro-therapy may be accurately targeted and the therapy zone is controllable, as a function of return electrode size, as well as frequency and current intensity.

The oscillator(s) in all the examples provide current of a few mA at voltages up to about 80 V, preferably at about 50 V, and the wave forms may be sinusoidal, square of sawtooth for example, most preferably sinusoidal, when contact feed electrodes are used, or sinusoidal or square wave, when capacitative feed electrodes are used.

It will be appreciated that it is not intended to limit the invention to the above example only, many variations, such as might readily occur to one skilled in the art, being possible, without departing from the scope thereof.

Thus, for example, one or both of the oscillators may be arranged to operate on a varying frequency during treatments, whereby the best frequency will vary and provide therapeutic treatment at other frequencies for example in the treatment of arthritic conditions.

Again for example, the oscillators may be operated intermittently to deliver bursts of energy simulating the effects of acupuncture without the need for needles.

Instead of providing two oscillators, a single oscillator may feed separate frequency dividers acting as independent frequency generators.

Although non-invasive techniques have been described, and indeed are preferred, it will be appreciated that one or more penetrative electrode(s), especially return electrode(s), could be employed.

The invention has been described in the foregoing examples primarily in relation to the provision of anaesthesia, especially during dental procedures but there are expected to be various other ways in which the apparatus can be used, some mentioned above, other examples being in physiotherapy, where muscles may be stimulated, suitably by low frequency waves or beats, for example 5-20 Hz, and in electro-stimulative brain procedures.

The reader's attention is directed to all papers and documents which are filed concurrently with this specification, and which are open to public inspection with this specification and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in the specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

While the best mode for carrying out the invention has been described in detail, those familiar with the art to which this invention relates will recognize various alternative designs and embodiments for practicing the invention as defined by the following claims.

What is claimed is:

1. Electro-therapy apparatus for providing therapeutic electric current to a treatment site of a patient, comprising means for providing two independent oscillating or pulsing electric alternating currents, of frequencies which differ from each other by up to about 250 Hz, but each being of frequency at least about 1 KHz, two feed electrodes respectively adapted to feed said electric currents to selected feed sites on or beneath the epidermal or mucous surface of the patient, and a return electrode common to said feed electrodes and adapted to be positioned on or beneath the epidermal or mucous surface of the patient, locally to said treatment site.

2. Electro-therapy apparatus according to claim 1, wherein said means for providing two electric currents comprises two independent oscillators.

3. Electro-therapy apparatus according to claim 1, wherein said means for providing two electric currents is adapted to provide two electric currents each of sinusoidal waveform.

4. Electro-therapy apparatus according to claim 1, having one return electrode only.

5. Electro-therapy apparatus according to claim 1, having two feed electrodes only.

6. Electro-therapy apparatus according to claim 1, comprising means for operating one or a plurality of feed electrodes on a varying frequency.

7. Electro-therapy apparatus according to claim 1, comprising means for operating feed electrodes intermittently.

8. Electro-therapy apparatus according to claim 1, comprising a casing for electrical components, and one or more capacitive feed electrodes located internally of the casing, the casing being an insulator and acting as a dielectric.

9. Electro-therapy apparatus according to claim 1, comprising one or more contact feed electrodes.

10. Electro-therapy apparatus according to claim 1, comprising a casing for electrical components and one or more capacitive feed electrodes located externally of the casing.

11. Electro-therapy apparatus according to claim 10, comprising a chair in which a capacitive feed electrode is located.

12. Electro-therapy apparatus according to claim 1, wherein the return electrode is adapted to be positioned on a gum adjacent a tooth to be treated.

13. Electro-therapy apparatus according to claim 1 wherein the summated area of the feed electrodes exceeds the area of the return electrode.

14. Electro-therapy apparatus according to claim 13, wherein said feed electrode summated area exceeds said return electrode summated area by a factor of more than 4.

15. Electro-therapy apparatus for providing therapeutic electric current to a treatment site of a patient, comprising means for providing two independent oscillating or pulsing electric currents, two feed electrodes, adapted respectively to feed said electric currents to selected feed sites on or beneath the epidermal or mucous surface of the patient, and a plurality of return electrodes common to the feed electrodes adapted to be positioned on or beneath the epidermal or mucous surface of the patient, adjacent to said treatment site, and means for switching the return electrodes into circuit sequentially.

16. Electro-therapy apparatus comprising:
    electrical circuitry apparatus for providing therapeutic electric current to a patient;
    a casing for said electrical circuitry apparatus; and
    one or more capacitive feed electrodes located internally of said casing.

17. Electro-therapy apparatus comprising:
    electrical circuitry apparatus for providing therapeutic electric current to a patient;
    a casing for said electrical circuitry apparatus;
    one or more capacitive feed electrodes located externally of said casing; and
    a chair in which a capacitive feed electrode is located.

18. Electro-therapy apparatus for providing a targeted therapeutic effect, which apparatus comprises:
    means for providing at least one therapeutic oscillating or pulsing electric current;
    at least one feed electrode adapted to feed said electric current to a selected feed site on or beneath the epidermal or mucous surface of the patient;
    and at least one return electrode adapted to be positioned on or beneath the epidermal or mucous surface of the patient, locally to said treatment site, wherein the area of the feed electrode, or summated area of the feed electrodes, when there is more than one, exceeds the area of the return electrode, or summated area of the return electrodes, when there is more than one (with reference to the electrodes which are operational at any given moment), by a factor of more than 4.

19. A method of therapy, comprising providing two feed electrodes, feeding via said feed electrodes two independent oscillating or pulsing electric currents to a patient, to respective selected feed sites on or beneath the epidermal or mucous surface of the patient, said currents each being of frequency at least about 1 KHz and differing from each other by up to about 250 Hz, and providing a return electrode common to said feed electrodes on or beneath the epidermal or mucous surface of the patient.

20. A method of therapy according to claim 19, herein the said frequencies differ by a frequency in the range about 60 to about 150 Hz.

21. A method of therapy according to claim 20, wherein the said frequencies differ by about 80 Hz.

22. A method of therapy according to claim 20, wherein the said frequencies differ by about 130 Hz.

23. A method of therapy according to claim 19, wherein each of the two feed electrodes operates at a frequency up to about 200 KHz.

24. A method of therapy according to claim 19, wherein each of the two frequencies is in the range about 4 to 5 KHz.

25. A method of therapy according to claim 19, wherein said feed electrodes are located at feed sites remote from said treatment site.

* * * * *